United States Patent [19]

Wesner

[11] Patent Number: 4,716,888
[45] Date of Patent: Jan. 5, 1988

[54] TINED LEADS

[75] Inventor: Walter H. Wesner, Plantation, Fla.

[73] Assignee: Cordis Corporation, Miami, Fla.

[21] Appl. No.: 918,669

[22] Filed: Oct. 16, 1986

Related U.S. Application Data

[63] Continuation of Ser. No. 744,949, Jun. 17, 1985, abandoned.

[51] Int. Cl.$^4$ ................................................ A61N 1/04
[52] U.S. Cl. ...................................... 128/785; 128/419 P
[58] Field of Search .............. 128/639, 641, 642, 644, 128/656, 657, 658, 772, 783, 784, 785, 786, 419 P, 419 D

[56] References Cited

U.S. PATENT DOCUMENTS

| | | | |
|---|---|---|---|
| 1,520,908 | 12/1924 | Meyer | 128/357 |
| 4,236,529 | 12/1980 | Little | 128/785 |
| 4,269,198 | 5/1981 | Stokes | 128/785 |
| 4,301,815 | 11/1981 | Doring | 128/786 |
| 4,407,303 | 10/1983 | Akerstrom | 128/786 |
| 4,409,994 | 10/1983 | Doring | 128/785 |
| 4,467,817 | 8/1984 | Harris | 128/785 |
| 4,506,679 | 3/1985 | Mann | 128/785 |
| 4,519,404 | 5/1985 | Fleischhacker | 128/786 |
| 4,549,557 | 10/1985 | Hakki | 128/642 |

FOREIGN PATENT DOCUMENTS

| | | | |
|---|---|---|---|
| 0085967 | 8/1983 | European Pat. Off. | 128/785 |
| 0126892 | 12/1984 | European Pat. Off. | 128/785 |

Primary Examiner—Edward M. Coven
Attorney, Agent, or Firm—George H. Gerstman

[57] ABSTRACT

A body-implantable lead includes an electrical conductor encased in inert, insulating material. The lead terminates at one end with an exposed electrode tip. A first set of tines is positioned about the lead nearest the electrode tip, the tines having a length less than the tines of a second set positioned about the lead and more remote from the electrode tip than the first set. The tines of the first set may also carry fins which extend toward the electrode tip to facilitate lead insertion. The tines may also be disposed in longitudinal or spiral rows along the lead.

9 Claims, 7 Drawing Figures

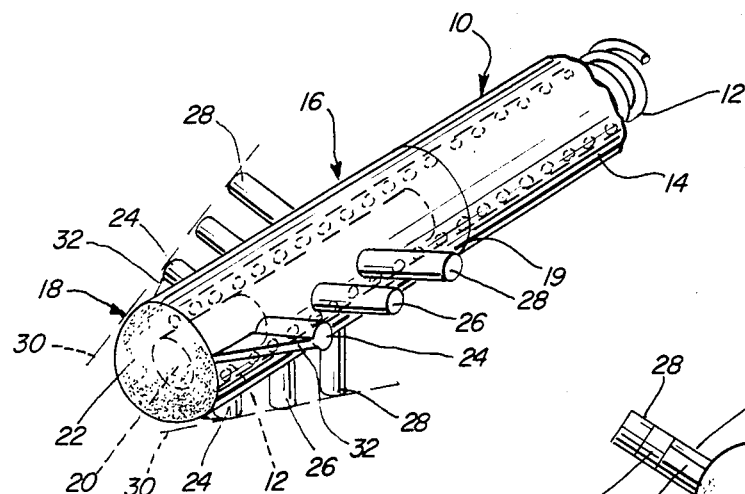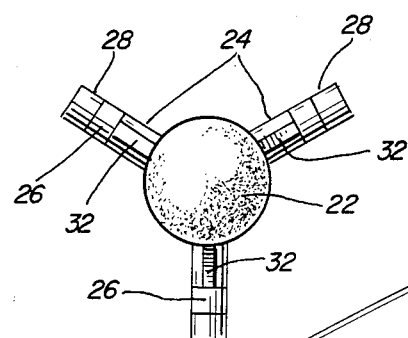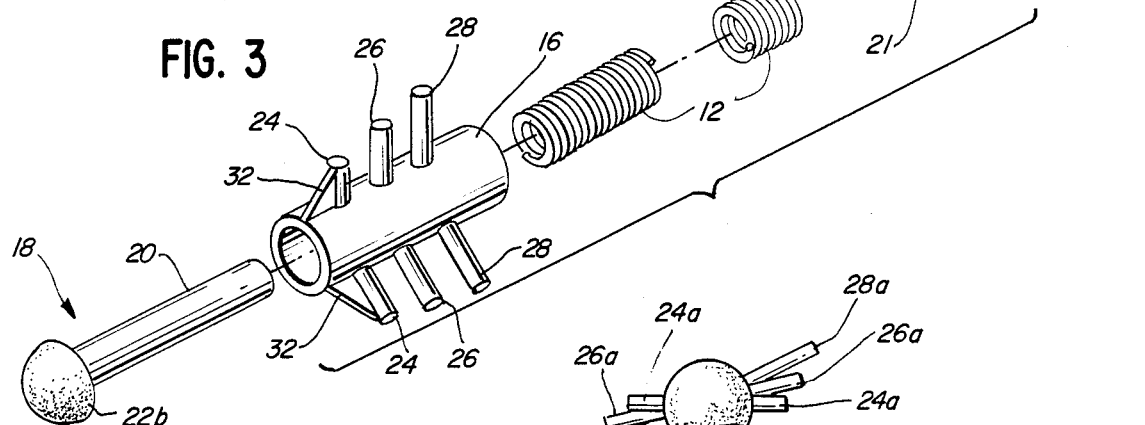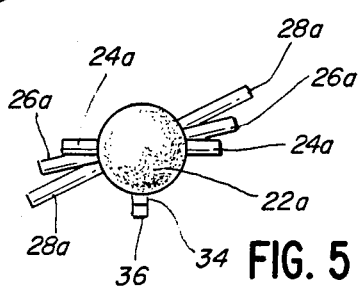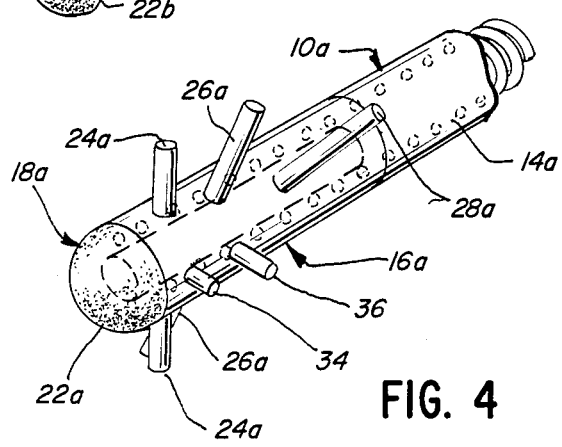

TINED LEADS

This application is a continuation of U.S. application Ser. No. 744,949, filed June 17, 1985, now abandoned.

BACKGROUND OF THE INVENTION

Some prior art pervenous leads have a plurality of outwardly extending tines disposed in a position closely adjacent to the electrode. The purpose of tines is to cooperate with the tissue of the heart, for example, and particularly the trabeculae found in the ventricles and the right atrial appendage, to retain the lead in position. Upon installation of the electrode and lead, the tines can become entangled with this or other tissue to assist in holding the electrode tip in its desired position.

BRIEF DESCRIPTION OF THE INVENTION

In this invention, a body-implantable lead such as a cardiac pacer lead comprises an electrical conductor encased in inert insulating material, with the lead terminating at its distal end with an exposed electrode tip. Non-conductive tines which may be made, if desired, as an integral part of the inert insulating material, are positioned adjacent the electrode tip, and extend outwardly from the lead.

In accordance with this invention, a first set of tines is positioned about the lead nearest the electrode tip. The tines of the first set have a length which is less than the tines of a second set, which second set of tines is positioned about the lead at a position more remote from the electrode tip than the first set.

A third set of tines may also be positioned about the lead at a position more remote from the electrode tip than the tines of the second set. The length of the tines of the third set may be greater than the length of the tines of the second set. Specifically, it is preferred for the outer ends of the tines of the first, second and third sets to occupy an imaginary substantially conical envelope defining an angle of 15° to 60° to the axis of the lead, although an angle of about 30° is preferred.

The tines are preferably perpendicular to the axis of the lead, although the tines may also assume other angular relationships to such axis, if desired.

The tines of the first set may carry fins which extend from the tines of the first set toward the electrode tip, and are connected to the inert insulating material encasing the electrical conductor. The presence of these fins facilitates the insertion of the lead through the trabeculae of the heart.

The tines may be positioned about the lead in longitudinal rows which are parallel to the lead axis. Alternatively, the tines may be positioned about the lead in rows that extend generally in a spiral path along the lead rather than in rows parallel to the lead axis.

By this invention, an electrode and retention assembly can provide improved ease of entrance into a position in a body organ such as the heart, where the tines enter into entangling or otherwise retaining relation with portions of the organ, for precise and permanent retention in a desired position so that the electrode can perform its intended function. Improved operation may be found with designs in accordance with this invention, when compared with those of the prior art.

BRIEF DESCRIPTION OF THE DRAWINGS

In the drawings, FIG. 1 is a fragmentary, enlarged perspective view of the end portion of a body-implantable lead made in accordance with this invention, with interior portions shown in dashed lines.

FIG. 2 is a front elevational view thereof.

FIG. 3 is an exploded, inverted perspective view thereof.

FIG 4 is a fragmentary, enlarged elevational view of another embodiment of the body-implantable lead of this invention.

FIG. 5 is a front elevational view of the lead of FIG. 4.

DESCRIPTION OF SPECIFIC EMBODIMENTS

Figure 6:
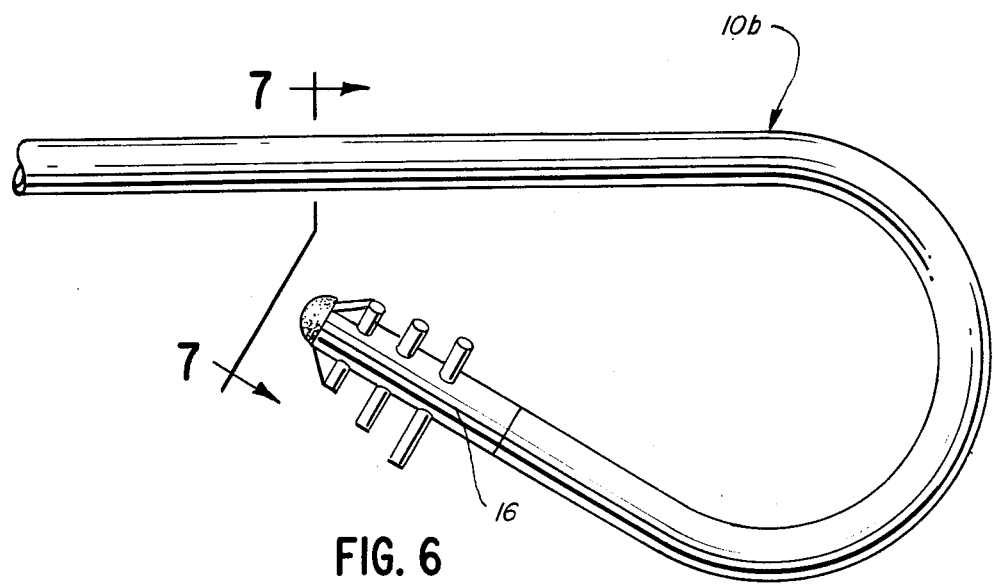
FIG. 6 is an enlarged side view of an end portion of a J-shaped body-implantable lead made in accordance with this invention.

Referring to FIGS. 1–3, the distal portion of an electrical lead 10 for implantation in the heart of a patient is disclosed. Cardiac pacer leads are well-known, and except as otherwise indicated herein, the lead 10 of this invention may be manufactured in the conventional manner.

The device is a tined pervenous lead. The terminal assembly which is inserted into the neck of the pacer is as all other pervenous leads. In the preferred embodiment, the lead is unipolar although the tines can be placed between two electrodes, a tip electrode and the band electrode, in the bipolar configuration. The lead is isodiametric or of uniform thickness throughout its length. Further, the lead can be inserted into the ventricle or the atrium but the ventricle is preferable.

Lead 10 comprises coiled electrical conductor wire or wires 12 which are encased in tubular insulating material 14. Insulating material 14 may be a silicone elastomer or polyurethane or any other appropriate material and may be of known design. Head portion 16 may be a molded piece of a silicone elastomer or polyurethane or the like including the tines, which will be discussed later. End 19 of head portion 16 abuts the end 21 (FIG. 3) of insulating tube 14.

Wire 12 communicates with metal electrode 18. Metal electrode 18 includes exposed head 22 and an integral shank portion 20 which is seen to by a cylindrical structure within head portion 16. Coiled wire 12 may be welded or otherwise frictionally held in electrical contact with the outer surface of shank portion 20. Head 22 of electrode 18 is desirably positioned in contact with a selected portion of the heart, so that electrical impulses pass through wire 12 to electrode 18 to stimulate and regulate heart action.

In accordance with this invention, various sets of tines 24, 26, 28 are carried on head portion 16. Tines 24, 26, 28 are shown to be in perpendicular relation to the axis of lead 10. It can be seen that the various sets of tines are of differing heights, with each set of tines 24, 26, 28 being distributed relatively equi-distantly about lead 10, so that each of the tines is spaced by about 120° from the other tines of its set. It can also be seen that each tine 26 is longer than each tine 24, and each tine 28 is longer than each tine 26 so that the entire array of tines all occupy an imaginary conical envelope as indicated by dotted lines 30 in FIG. 1. In other words, in the preferred embodiment an imaginary cone could fit over the end of lead 10, and would touch the ends of all of tines 24, 26, 28 without bending or distortion. Preferably, this imaginary conical envelope defines an angle of about 30° to the axis of lead 10 although the angle can be from 15° to 60° to the axis of lead 10. When the angle approaches 60°, the differential height between the respective tines 24, 26, 28 is quite substantial, but when the conical angle is only about 15°, the differential height between the tine is substantially less. Preferably the differential in height between adjacent tines 24, 26, and adjacent tines 26 and 28 is substantially the same, as shown in FIG. 2.

Tines 24, 26 and 28 may be made of a relatively soft material such as a silicone elastomer or polyurethane. The tines are preferably an integrally molded part of molded head portion 16 through which electrode 18 fits. Insulating material 14, head portion 16 and electrode 18 may be glued together with an appropriate medical grade adhesive. Electrode 18 may be made out of conventional alloys which are suitable for the manufacture of biomedical electrodes.

Each of tines 24 of the first set may carry a fin 32 which extends from each tine 24 toward the head 22 of electrode 18. The thickness of each fin 32 is less than the thickness (diameter) of a tine. Fins 32 may also be connected to the forward surface of each tine 24, and also to the body of head portion 16 as shown in FIGS. 1 and 3. Fins 32 may be an integrally molded part of head portion 16.

One purpose of fins 32 is to facilitate the insertion of lead 10 through the trabeculae of the heart by pushing them up and over the outer ends of tines 24 as lead 12 is advanced into its desired position. The trabeculae then may fall between adjacent tines 24, 26 in a given row of tines, or between tines 26, 28 in the same row, resulting in the entrapment and entanglement of the distal end of lead 10, for permanent emplacement of the electrode 18 at a desired location.

The use of the fin 32 and the graduation in height of the tines has a distinct advantage in lead insertion. With tines of uniform length and, usually long such as in the last row of this device, it is necessary to "over insert" the lead. Thus, the lead must be advanced further than may be desirable so the longer tine can become trapped within the trabeculae. This over insertion is negated or minimized with a lead whose tines are graduated in length with the shortest tine adjacent to the tip electrode 22.

It can thus be seen that the multiplicity of tines aids in the engagement of the lead with the trabeculae. By staggering the tines as described and illustrated, there is some engagement with the smaller tines 24 and even more engagement as the lead moves toward the heart wall.

While the specific embodiment of FIGS. 1–3 shows a lead having sets of tines in longitudinal array placed around the lead at approximately 120° spacing, it is contemplated that four or more tines may be placed in each of the sets, so that the spacing between tines of a set around the lead is 90° in the case of four tines per set, and even less spacing if it is desired for more than four tines to be used in each set.

While the tines of the respective sets are shown to be placed in linear array and in longitudinal relation to the axis of the lead 10, FIGS. 4 and 5 show a variant structure for a lead of this invention, in which the tines may be placed in a generally spiral path about the lead.

As shown in FIGS. 4 and 5, lead 10a may be identical in structure to lead 10 except as otherwise disclosed herein. Coiled electrical wire 12a and insulation 14a are present as in the previous embodiment, with the electrical wire communicating with electrode 18a. Head portion 16a may be molded as in the previous embodiment, with electrode 18a being placed inside with electrode head 22a exposed, and the entire assembly glued together with appropriate adhesive, for example, medical grade silicone adhesive.

As before, the projecting tines form first, second and third sets. Tines 24a comprise a first set; tines 26a a second set; and tines 28a a third set. In this instance, only a pair of diametrically opposed tines is present in each set.

As previously, tines 26a are longer than tines 24a, while tines 28a are longer than tines 26a. Tines 24a, 26a and 28a may all have ends that fit within a conical envelope as in the previous embodiment.

As a difference from the previous embodiment, in FIG. 4 tines 24a, 26a and 28a form rows, but the rows are not parallel to the lead axis as in the previous embodiment. Rather, they extend generally in a spiral path along lead 10a as shown in FIG. 4.

Additionally, a pair of short tines 34, 36 are provided between the spiral rows of tines 24a, 26a, 28a. These tines may be shorter than the former tines, and may define a line parallel to the axis of lead 10a. If desired, another set of short tines may be placed in a position about 180° around the lead from the position of tines 34, 36 as shown. Also, tines 36 may be slightly longer than tines 34. If desired, fins similar to fins 32 may be added to tines 24a and 34.

Figure 7:
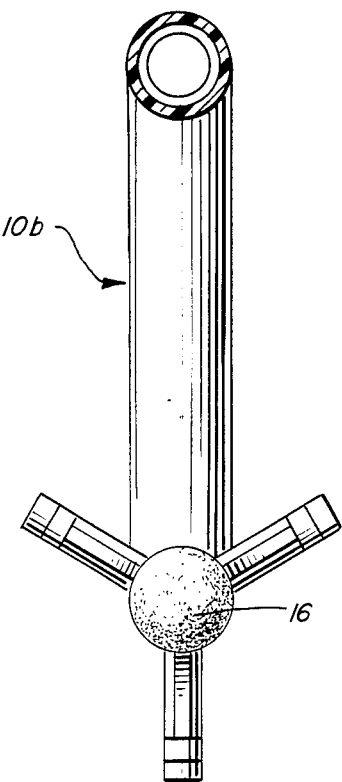
FIG. 7 is a cross-sectional view thereof, taken along the plane of the line 7—7 of FIG. 6.

In FIGS. 6 and 7, a J-shaped lead 10b is illustrated, preferably for use in the atrial chamber. The J-shaped lead 10b is shown with a head 16 that is identical to head 16 of the FIGS. 1–3 embodiment. However, the heads of other embodiments may be used with the J-shaped lead 10b, if desired.

Accordingly, the tined lead of this invention provides significant improvements in operation, being easily installed into position, with tines that provide good entanglement of the electrode in a desired position.

The above has been offered for illustrative purposes only, and is not intended to limit the scope of the invention of this application, which is as defined in the claims below.

What is claimed is:

1. A body-implantable lead which comprises:
an elongated electrical conductor encased in an elongated tube comprising inert insulating material, said lead terminating at one end with an exposed electrode tip;
a first set of discrete extending projections which extend outwardly from said elongated tube;
a second set of discrete extending projections which extend outwardly from said elongated tube;
the space between said first set and said second set being free from all transverse material that is capable of contacting the trabeculae;
said first set of discrete extending projections having a length that is less than the length of said second set of discrete extending projections; and
said second set of discrete extending projections being positioned more remote from said electrode tip than said first set of discrete extending projections.

2. A body-implantable lead as described in claim 1, in which the projections of said first set carry fins which extend from the projections of the first set toward the electrical tip, and are connected to the inert insulating material encasing the electrical conductor, to facilitate insertion of the lead through the trabeculae of the heart.

3. A body-implantable lead as described in claim 1, including a third set of discrete extending projections which extend outwardly from said elongated tube, said third set of discrete extending projections having a length that is greater than the length of said second set of discrete extending projections and said third set being positioned more remote from said electrode tip than said second set.

4. A body-implantable lead as described in claim 3, in which the outer ends of the projections of the first, second and third sets all occupy an imaginary conical envelope defining an angle of 15° to 60° to the axis of said lead.

5. A body-implantable lead as described in claim 1, in which said projections are perpendicular to the axis of said lead.

6. A body-implantable lead as described in claim 1, in which said projections are positioned about said lead in longitudinal rows parallel to the lead axis.

7. A body-implantable lead as described in claim 1, in which the projections are positioned about said lead in rows that extend generally in a spiral path along said lead.

8. A body-implantable lead as described in claim 1, in which the lead is a J-shaped atrial lead.

9. A body-implantable lead which comprises:

an elongated electrical conductor encased in an elongated tube comprising inert insulating material, said lead terminating at one end with an exposed electrode tip;

a first set of discrete extending projections which extend outwardly from said elongated tube;

a second set of discrete extending projections which extend outwardly from said elongated tube;

a third set of discrete extending projections which extend outwardly from said elongated tube;

said first set having a length that is less than the length of said second set;

said second set having a length that is less than the length of said third set;

said third set being positioned more remote from said electrode tip than said second set;

the space between the first set and the second set and the space between the second set and the third set being free from all transverse material that is capable of contacting the trabeculae;

said second set being positioned more remote from said electrode tip than said first set;

the projections of said first set carrying fins which extend from the projections of the first set toward the electrode tip, and are connected to the inert insulating material encasing the electrical conductor, to facilitate insertion of the lead through the trabeculae of the heart;

the outer ends of the projections of the first, second and third sets all occupying an imaginary conical envelope defining an angle of 15° to 60° to the axis of said lead; and said projections being perpendicular to the axis of said lead.

* * * * *